United States Patent
Connors et al.

(10) Patent No.: US 9,962,309 B2
(45) Date of Patent: May 8, 2018

(54) THERMAL MASSAGE APPARATUS

(71) Applicant: BioActive Sports, Rochester, NY (US)

(72) Inventors: Antoine B. Connors, Rochester, NY (US); James C. Newton, Rochester, NY (US)

(73) Assignee: Bioactive Sports, Rochester, NY (US)

( * ) Notice: Subject to any disclaimer, the term of this patent is extended or adjusted under 35 U.S.C. 154(b) by 395 days.

(21) Appl. No.: 14/662,815

(22) Filed: Mar. 19, 2015

(65) Prior Publication Data

US 2015/0265457 A1     Sep. 24, 2015

Related U.S. Application Data

(60) Provisional application No. 61/955,727, filed on Mar. 19, 2014.

(51) Int. Cl.
| | |
|---|---|
| *A61H 7/00* | (2006.01) |
| *A61F 7/00* | (2006.01) |
| *A61H 1/00* | (2006.01) |
| *A61H 15/00* | (2006.01) |
| *A61H 15/02* | (2006.01) |
| *A61F 7/10* | (2006.01) |

(52) U.S. Cl.
CPC .......... *A61H 1/008* (2013.01); *A61H 15/0092* (2013.01); *A61H 15/02* (2013.01); *A61F 2007/108* (2013.01); *A61H 2015/0064* (2013.01); *A61H 2201/0214* (2013.01); *A61H 2201/0257* (2013.01)

(58) Field of Classification Search
CPC ........ A61H 7/001; A61H 7/002; A61H 7/003; A61H 15/00; A61H 2201/0153; A61H 15/02; A61H 15/0085; A61H 15/0092; A61H 2015/0014; A61H 2201/0214; A61H 2201/0257; A61H 2201/1253; A61H 2205/021; A61H 2015/0042; A61H 2201/0207; A61H 1/008; A61H 39/00; A61H 39/04; A61H 39/06; A61F 7/00; A61F 7/08; A61F 2007/0268; A61F 2007/0088; A61F 2007/108; A61F 2007/0087
USPC ........................................ D24/200, 211, 214
See application file for complete search history.

(56) References Cited

U.S. PATENT DOCUMENTS

| | | | | |
|---|---|---|---|---|
| 2,017,400 | A * | 10/1935 | Hoyer ................ | A61H 7/00 601/118 |
| 3,382,866 | A * | 5/1968 | Harris ................ | A61F 7/02 219/240 |
| D277,983 | S * | 3/1985 | Kaminski ................ | D24/214 |
| 5,170,778 | A * | 12/1992 | Jamis ................ | A61H 15/00 601/121 |
| 5,284,272 | A * | 2/1994 | Wei ................ | A61H 7/00 222/192 |
| D346,866 | S * | 5/1994 | Lotuaco ................ | D24/200 |
| 5,389,063 | A * | 2/1995 | Wu ................ | A61H 7/001 273/153 S |
| 5,413,551 | A * | 5/1995 | Wu ................ | A61H 15/00 601/131 |

(Continued)

*Primary Examiner* — Rachel T Sippel
*Assistant Examiner* — Christopher Miller
(74) *Attorney, Agent, or Firm* — Burns & Levinson LLP; George N. Chaclas; Katherine M. Larson

(57) ABSTRACT

A multi-component, convertible, individual thermal therapeutic device has multiple parts that can be arranged in at least 3 ways to provide multiple therapeutic treatments to the users body.

20 Claims, 12 Drawing Sheets

(56) References Cited

U.S. PATENT DOCUMENTS

| | | | | |
|---|---|---|---|---|
| 5,628,772 A | * | 5/1997 | Russell | A61F 7/10 601/112 |
| D386,879 S | * | 11/1997 | Daniels | D24/214 |
| 5,735,803 A | * | 4/1998 | Musilli | A61H 15/0092 601/128 |
| 5,843,005 A | * | 12/1998 | Chubinsky | A61H 7/003 601/135 |
| 6,077,239 A | * | 6/2000 | Lin | A61H 7/003 601/134 |
| 6,102,876 A | * | 8/2000 | Winger | A61H 15/0092 601/107 |
| 6,113,530 A | * | 9/2000 | Chien | A61H 39/00 600/9 |
| 6,267,738 B1 | * | 7/2001 | Louis | A61H 1/008 601/118 |
| 6,299,585 B1 | * | 10/2001 | Yoo | A61H 7/001 601/118 |
| 6,432,071 B1 | * | 8/2002 | Hsieh | A61H 23/0263 601/131 |
| D586,469 S | * | 2/2009 | Henry | D24/200 |
| 8,226,699 B2 | * | 7/2012 | Evans | A61F 7/02 607/108 |
| D683,862 S | * | 6/2013 | Hartman | D24/214 |
| D684,702 S | * | 6/2013 | Cho | D24/215 |
| 2004/0249322 A1 | * | 12/2004 | Cohen | A61H 7/001 601/131 |
| 2005/0061829 A1 | * | 3/2005 | Tsaur | A45D 40/26 222/1 |
| 2008/0139981 A1 | * | 6/2008 | Walquist | A61H 7/001 601/134 |
| 2009/0234182 A1 | * | 9/2009 | Buchholz | A61H 19/44 600/38 |
| 2009/0264971 A1 | * | 10/2009 | Wickstead | A61F 7/03 607/108 |
| 2009/0306560 A1 | * | 12/2009 | Lund | A61H 7/003 601/135 |
| 2011/0040361 A1 | * | 2/2011 | Levy | A61F 7/00 607/114 |
| 2011/0054369 A1 | * | 3/2011 | DeStefano | A61H 7/001 601/135 |
| 2012/0265108 A1 | * | 10/2012 | Young | A61F 7/03 601/15 |
| 2012/0310120 A1 | * | 12/2012 | Orlando | A61H 7/003 601/15 |
| 2013/0138024 A1 | * | 5/2013 | Jennings | A61H 15/0092 601/119 |

\* cited by examiner

THERMAL MASSAGE APPARATUS

CROSS-REFERENCE TO RELATED APPLICATION

This application is based on and claims the benefit of U.S. Provisional Patent Application No. 61/955,727, filed Mar. 19, 2014, which is incorporated herein by reference.

TECHNICAL FIELD

The present disclosure relates to a thermal therapeutic product, and more particularly, to a thermal therapeutic massage apparatus for massaging various human body parts to stimulate increased rehabilitation in the human body.

BACKGROUND

In general, massage devices, as are known, primarily include objects for use by an injured person or rehabilitation professional in deep tissue massage. These massage devices are used to rehabilitate injuries to a human body such as relieve muscle aches and sore muscles, promote blood circulation, relieve muscle cramps, and loosen tight and knotted muscles. Further, massage devices also reduces the amount of strain upon the injured person or massage therapist while attempting to rehabilitate injuries. These massage devices can be as simple as heated stones or as complex as tools with complexly formed protrusions for the kneading of fascia and other such connective tissue.

In addition, the use of ice packs or another cold material is common for the effective treatment of bleeding, pain and swelling injuries to the human body. When ice is applied to the affected area in the first hours after injury, swelling of the injury is reduced, thereby also reducing pain. Bleeding is also substantially minimized as local blood vessels are constricted by the application of cold temperatures to the injury.

However, these massage devices may not be able to provide the benefits associated with the application of ice or another substantially cold material to injured areas. In addition, using ice packs and other cold frozen materials may result in frostbite to injured areas since the ice packs often stay stationary on the injured areas. Further, the use of ice packs may not provide the remodeling of damaged tissue through massage alone.

SUMMARY

An aspect of the present disclosure provides a thermal massaging apparatus that stimulates injury rehabilitation. According to an exemplary embodiment of the present disclosure, a thermal massaging apparatus includes a body that has complimentary halves having an exterior surface surrounding an interior surface, the interior surface defining a first interior, a first mounting frame extending from the interior surface of a first complimentary half, a second mounting frame opposing the first mounting frame and extending from the interior surface of a second complimentary half, an elongated rod extending from within the first mounting frame to within the second mounting frame, the elongated rod defining a second interior, a first O-ring on a first end of the elongated rod within the first mounting frame, a second O-ring on a second end of the elongated rod within the second mounting frame so that the first and second O-rings are compressed to retain the complimentary halves together, and a filler material that retains cold temperature within at least one of the first and second interiors.

According to another exemplary embodiment of the present disclosure, a thermal massaging apparatus may include a body that may have an exterior surface that surrounds an interior surface, a first mounting frame that extends from the interior surface, a second mounting frame that opposes the first mounting frame and extends from the interior surface, an elongated rod that extends between the first mounting frame and the second mounting frame, and a filler material that retains cold temperature in at least one of a first and second interiors. The first interior may be defined by the interior surface of the body. In addition, the second interior may be defined by the elongated rod.

Further, the body may include a female portion that defines a circumferential groove adjacent an edge of the female portion and a male portion that defines a circumferential ridge adjacent an edge of the male portion wherein the edges may be configured to align so that the circumferential ridge selectively couples in the circumferential groove to retain the portions together. In addition, a shape of the portions may be selected from the group consisting of hemispherical, a cross-sectional trapezoidal shape, a flattened pyramid, a cross-sectional rectangular shape and combinations thereof. The body may also include a first hemisphere and a second hemisphere that threads to the first hemisphere to selectively enclose the interior.

The first mounting frame may include a first circular flange and the second mounting frame may include a second circular flange. Additionally, the elongated rod may include a tube that has a first end that has a convex shape for massaging a first type of body contour that is inserted into the first circular flange and a second end having a concave shape for massaging a complementary type of body contour that is inserted into the second circular flange.

Further, the elongated rod may include a first O-ring adjacent to the first end of the elongated rod and a second O-ring adjacent to the second end of the elongated rod. In addition, the body may be spherical and the tube may extend along an axis on a maximum diameter of the body.

According to another exemplary embodiment of the present disclosure, a thermal massaging rod may include a first end that has a convex shape and a second end having a concave shape so that, depending upon the shape of the tissue needing massage, one end of the massaging rod is complementarily shaped. The thermal massaging rod defines an interior that may also include a filler material that retains cold when exposed to cold temperatures. Further, the thermal massaging rod may include a sleeve wrapped around a substantial middle portion of the thermal massaging rod.

It should be appreciated that the subject technology can be implemented and utilized in numerous ways, including without limitation as a process, an apparatus, a system, a device, a method for applications now known and later developed. These and other unique features of the methods and systems disclosed herein will become more readily apparent from the following description and the accompanying drawings.

BRIEF DESCRIPTION OF THE DRAWINGS

The features of the present invention will best be understood from a detailed description of the invention and example embodiments thereof selected for the purposes of illustration and shown in the accompanying drawings in which.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Hereinafter, exemplary embodiments of the present disclosure will be described in detail with reference to the accompanying drawings so that those skilled in the art to which the present disclosure pertains can easily carry out the present disclosure.

Figure 1A:
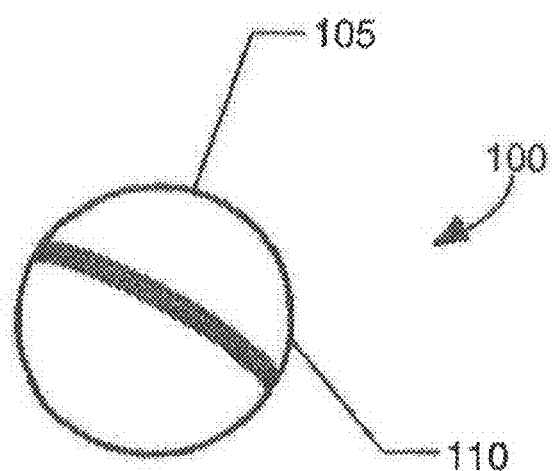
FIGS. 1A and 1B are exemplary views showing a shape of a massager according to an embodiment of the present disclosure.
Figure 1B:
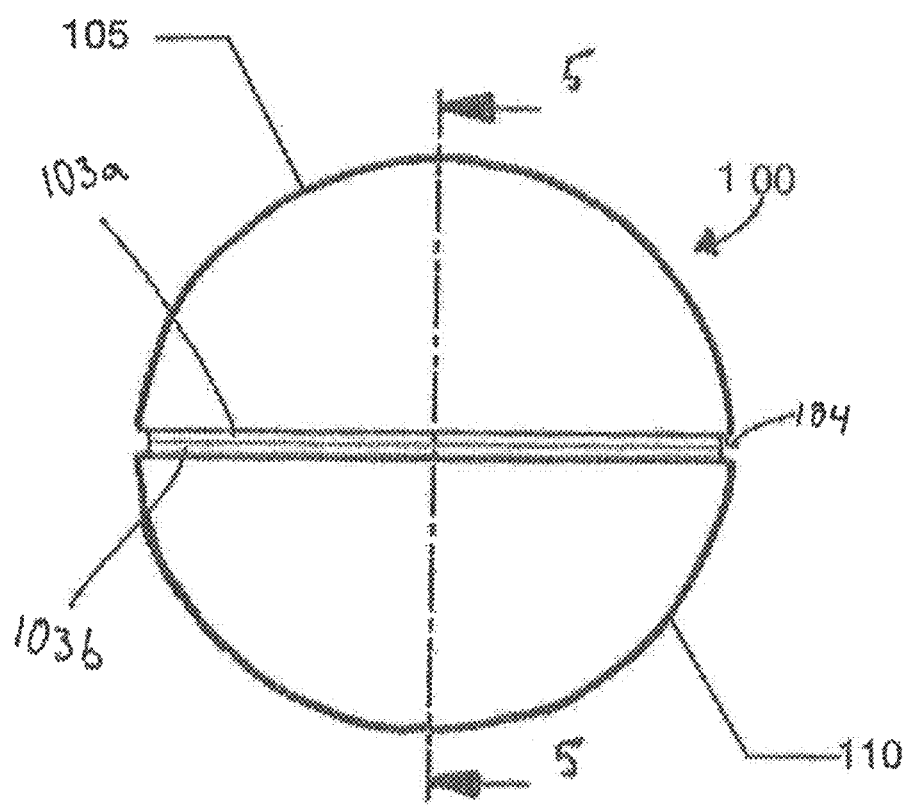

As illustrated in FIGS. 1A and 1B, a thermal massaging apparatus is shown and referred to generally by the reference numeral 100. The thermal massaging apparatus 100 provides users and professionals with an easy to use, adaptable manual apparatus 100 for applying pressure and cooling to area of the body in need of massage. Alternatively, the thermal massaging apparatus 100 applies heat and pressure.

The thermal massaging apparatus 100 includes a body 105. The body 105 includes two hemispheres or shells 101, 102, each with an exterior surface 110 and an interior surface 250 (see FIG. 2). The body 105 can be made from plastic, metal, wood or other materials and combinations thereof. Preferably, the body 105 is made from a material that efficiently conducts thermal energy, be it relatively hot or cold. The exterior surface 110 is handled by the user so preferably the exterior surface 110 has a pleasant tactile feel. Tacky rubber features, such as nubs or ridges, may be formed on the exterior surface 110 to enhance the tactile feel.

Still referring to FIG. 1, the hemispheres 101, 102 are slightly separated. A pair of foam washers 103a, 103b fill the gap 104 between the hemispheres 101, 102.

Figure 2:
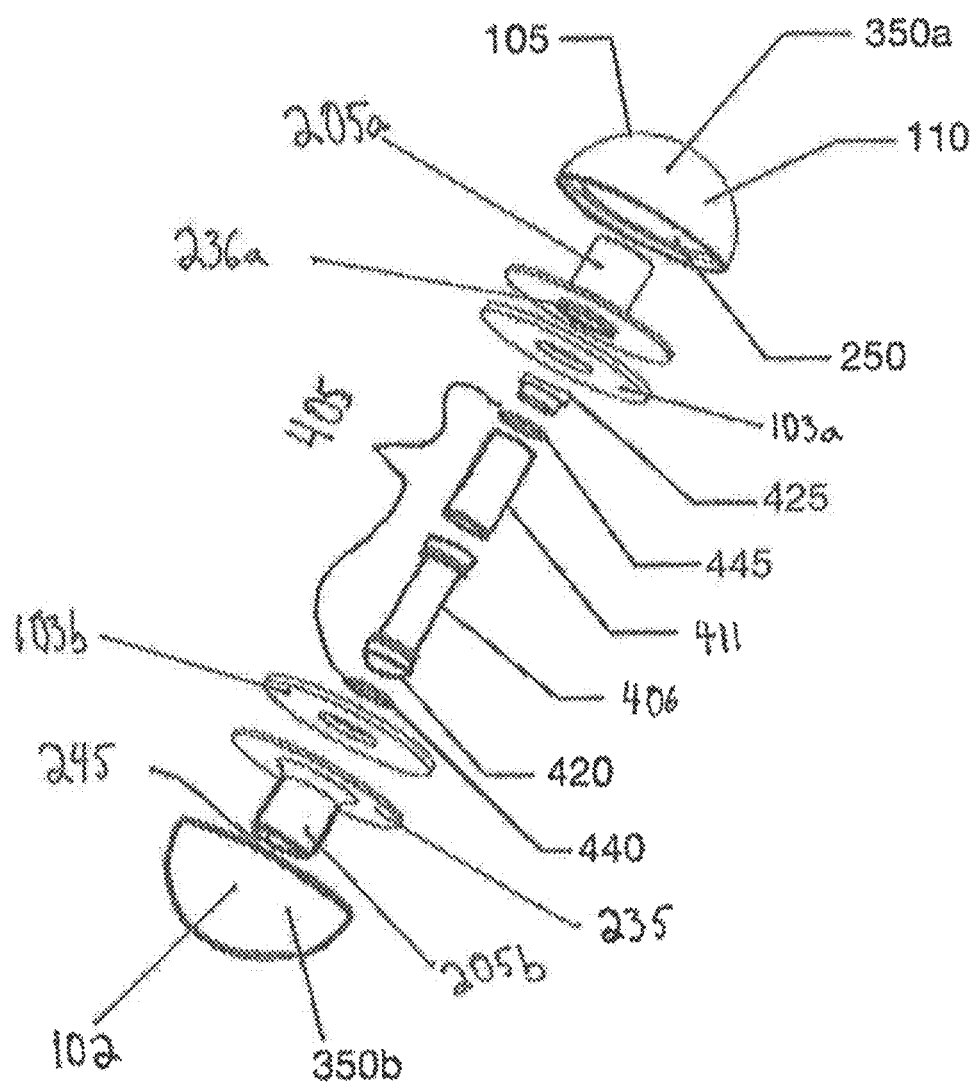
FIG. 2 is an exploded view of the embodiment of the present disclosure as shown in FIGS. 1A and 1B.

Referring now to FIG. 2, an exploded view of the thermal massaging apparatus 100 is shown. When assembled, the hemispheres 101, 102 include opposing first and second mounting frames 205a, 205b that extend inward. Each mounting frame 205a, 205b has a proximal base 245a, 245b that terminates in a circular distal flange 235a, 235b. Inwardly upstanding from the flanges 235a, 235b are shoulders 236a, 236b. The mounting frames 205a, 205b and the hemispheres 101, 102 are shown as separate but may be integrally formed by 3D printing and the like.

An elongated rod 405 extends between the first mounting frame 205a and the second mounting frame 205b. The elongated rod 405 provides a cooling effect to the thermal massaging apparatus 100. Alternatively, the elongated rod 405 provides a heating effect to the thermal massaging apparatus 100. The elongated rod 405 may also be used separately as a stand-alone massaging device.

The elongated rod 405 has a tubular body 406 with a convex end 420 and a concave end 425. The ends 420, 425 sealingly engage the tubular body 406. One or both of the ends 420, 425 may be selectively removed to allow filling the tubular body 406. An O-ring 440, 445 mounts on each end 420, 425 as described in more detail below. The tubular body 406 is wrapped or surrounded by a foam tube 411 for providing insulation and a pleasant surface for gripping when the rod 405 is used independently. The differently shaped ends 420, 425 are particularly useful for effectively massaging different body parts.

The thermal massaging apparatus 100 contains a filler material 410 that retains cold temperature to provide cooling effects while using the thermal massaging apparatus 100. Alternatively, the thermal massaging apparatus 100 contains a filler material 410 that retains hot temperature to provide heating effects while using the thermal massaging apparatus 100. The filler material 410 may be contained within an interior 407 (see FIG. 5) of the tubular body 406 of the elongated rod 405 and/or within an interior 109 (see FIG. 5) defined between the hemispheres 101, 102.

Figure 3:
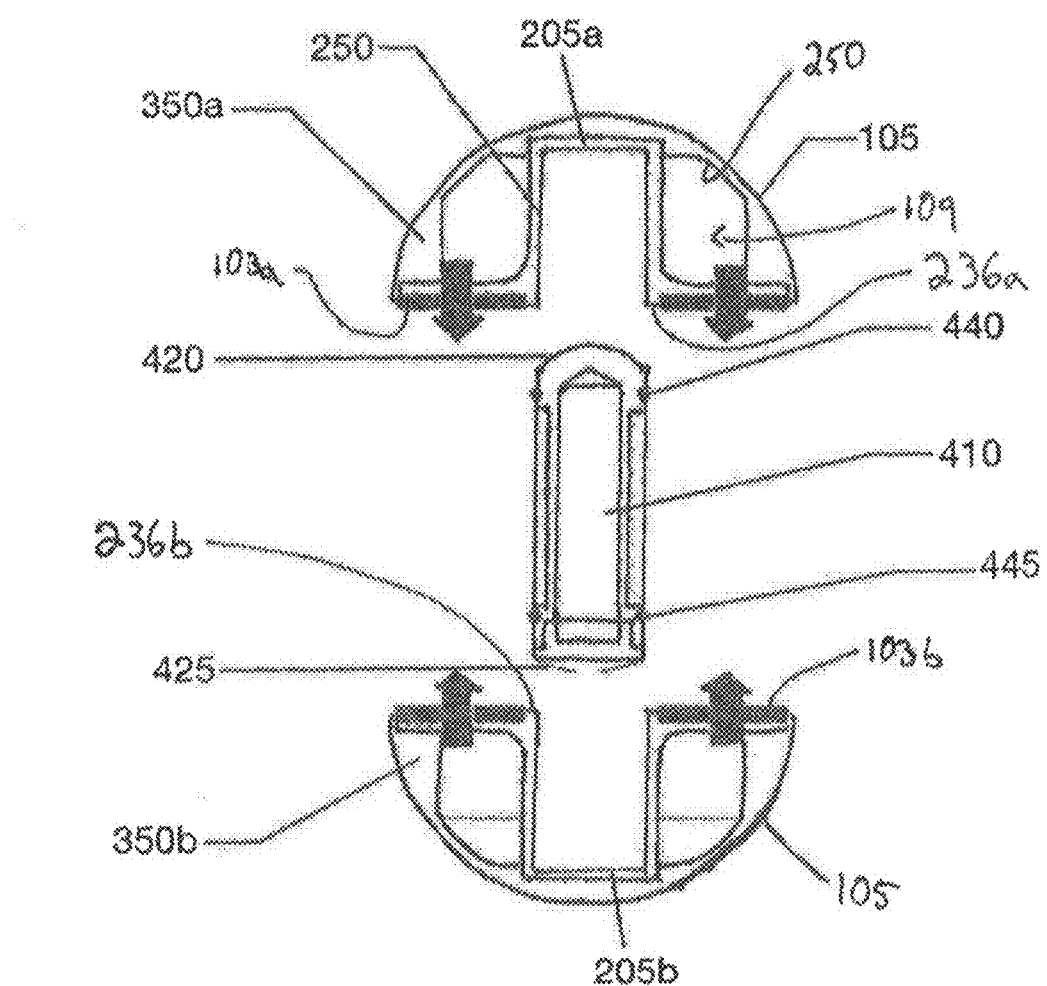
FIG. 3 is a cross-sectional view of the embodiment as shown in FIGS. 1A and 1B prior to assembly.
Figure 4:
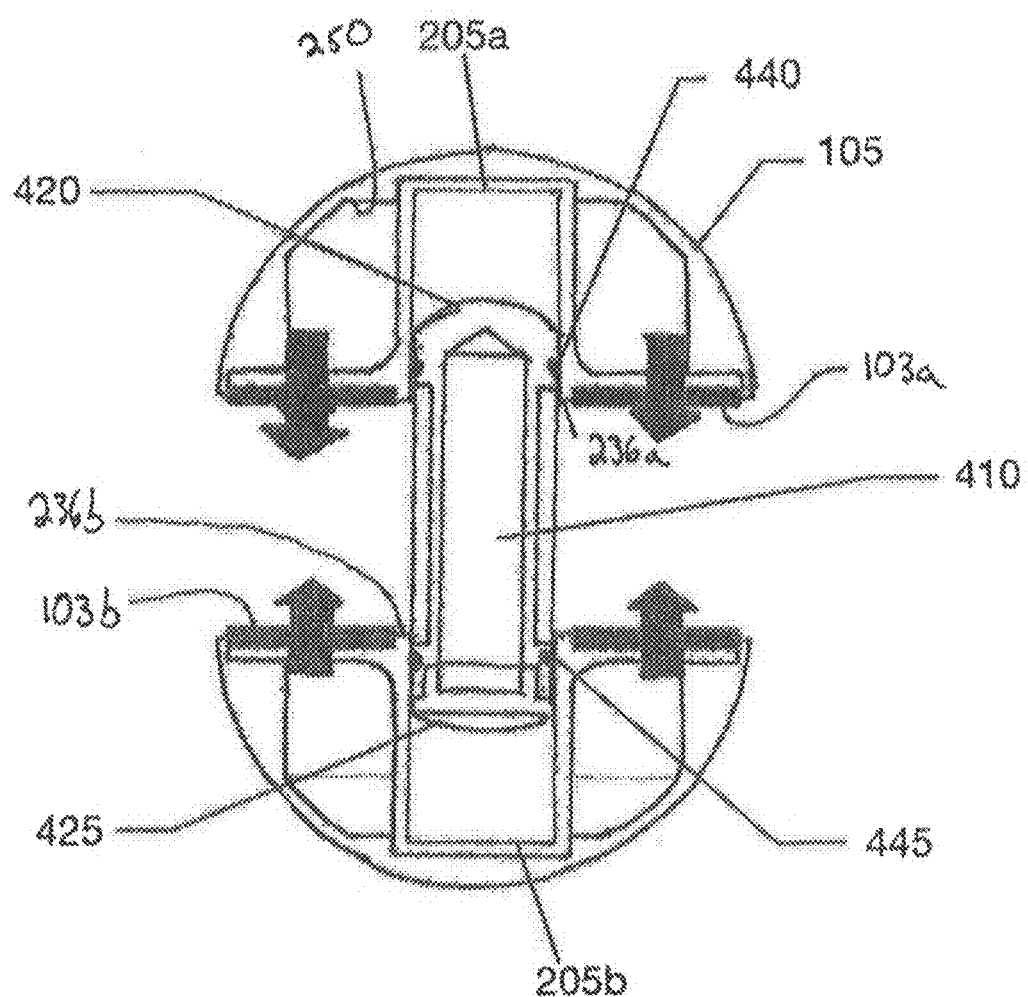
FIG. 4 is a cross-sectional view of an intermediate assembly position of the embodiment as shown in FIGS. 1A and 1B.
Figure 5:
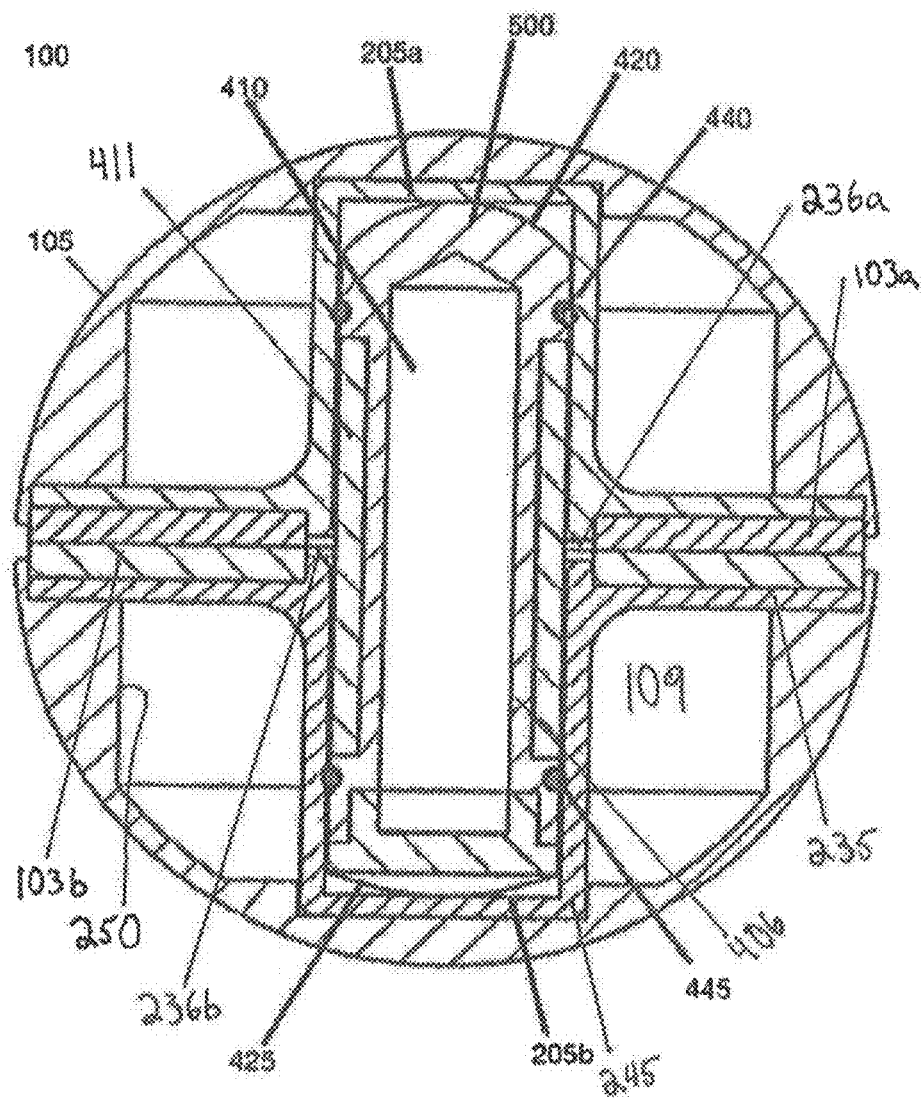
FIG. 5 is an exemplary cross-sectional view taken along line 5-5 of FIG. 1B.
Figure 6:
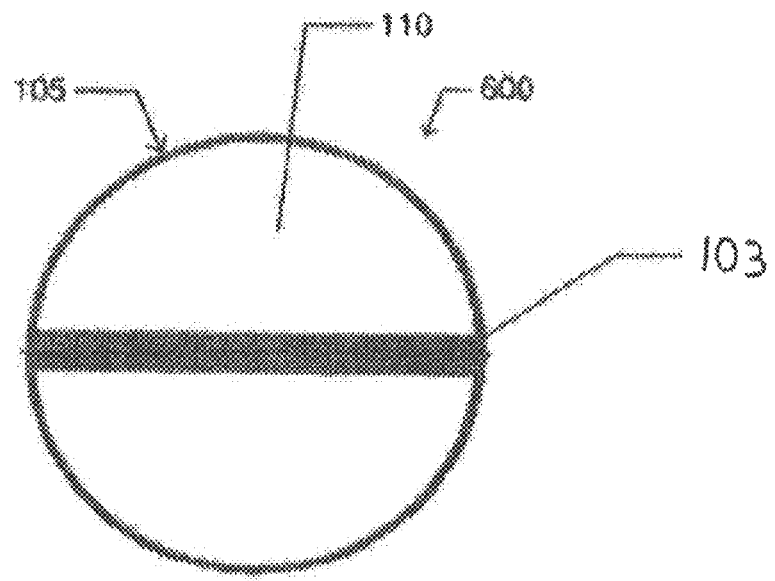
FIG. 6 is an exemplary view of a thermal massage apparatus according to an embodiment of the present disclosure that includes a foam washer.
Figure 7:
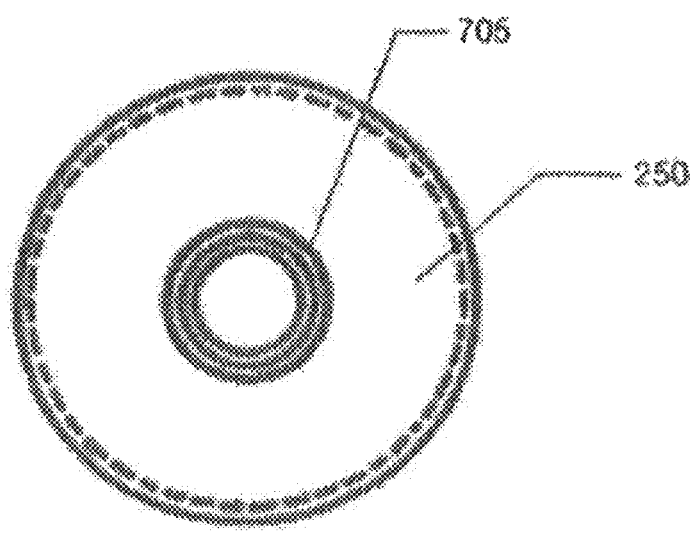
FIG. 7 is a side view of one half of a body of a thermal massage apparatus according to an embodiment of the present disclosure.
Figure 8:
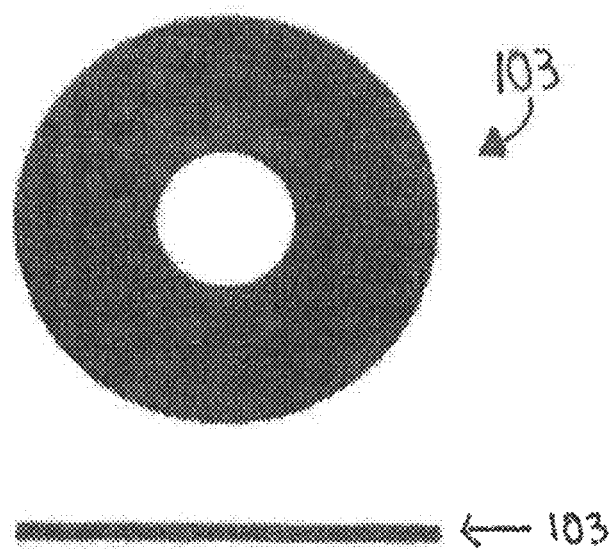
FIG. 8 is a top and side view of a foam washer that is coupled with a half of a body of a thermal massage apparatus according to an embodiment of the present disclosure.

As shown in FIGS. 3 to 5, the thermal massaging apparatus 100 is shown in cross-sectional view in progressive stages of assembly. In FIG. 3, complimentary halves 350a, 350b are separate and the elongated rod 405 is fully assembly with thermal filler material 410. Thermal filler material 410, insulation or temperature conducting material may also be included in the interior 109.

The first mounting frame 205a extends from the interior surface 250 of a first complimentary half 350a. A second mounting frame 205b opposes the first mounting frame 215 and extends from the interior surface 250 of a second complimentary half 350b. When assembly as in FIG. 5, the elongated rod 405 extends from within the first mounting frame 205a to within the second mounting frame 205b.

To retain the halves 350a, 350b together, the first and second O-rings 440, 445 are compressed between the mounting frames 215, 220 and the elongated rod 405. An external force is applied (e.g., when a user pulls the complementary halves apart) so that the elongated rod 405 can be placed in a refrigerator for cooling or a microwave for heating and the like or stand-alone use. The O-rings 440, 445 are housed within circumferential recesses 1505a, 1505b (see FIG. 15) formed on the convex end 420 and the concave end 425. The circumferential recesses 1505a, 1505b allow for the O-rings 440,445 to be held in place when the halves 350a, 350b are being assembled.

Turning to FIGS. 6-10, additional embodiments of the massager of the present disclosure are indicated generally by the reference numerals 600, 900. The massagers 600, 900 are very similar to the massagers described above, and therefore, like reference numerals are used to indicate like elements. The primary difference of the massagers 600, 900 in comparison to the massagers above is the mounting structure. Screw threads 705 may be used to attach the elongated rod 405 into the mounting frame 205 (see FIG. 7).

Figure 9:
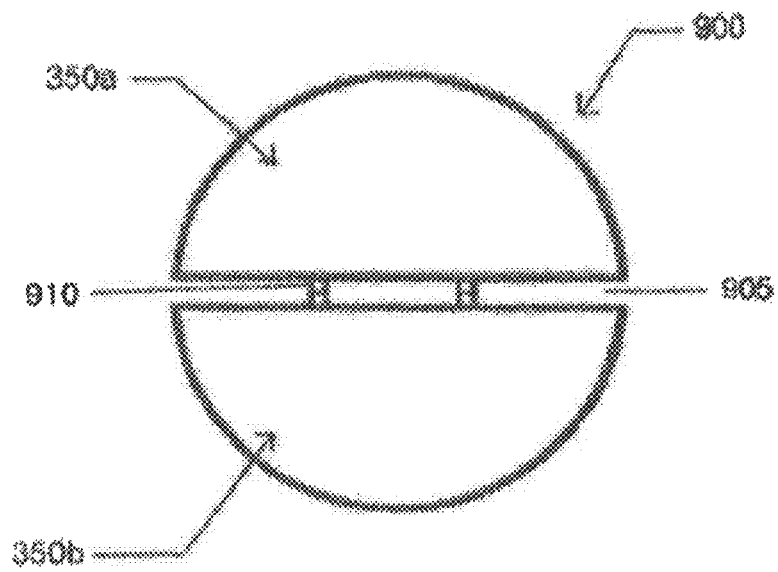
FIG. 9 is an exemplary view of the thermal massage apparatus showing a gap between halves according to an embodiment of the present disclosure.
Figure 10:
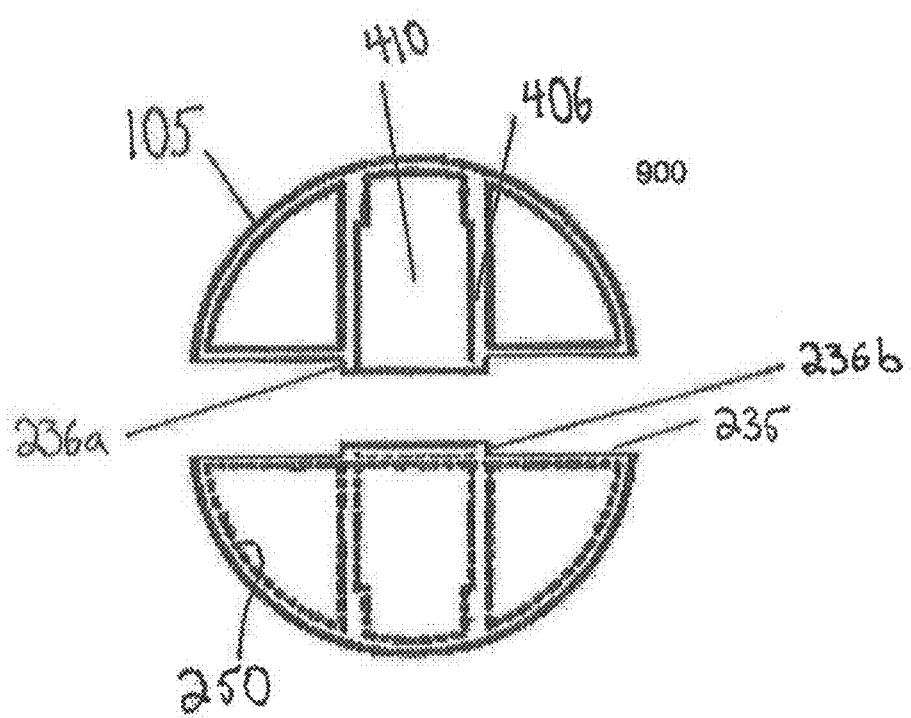
FIG. 10 is a cross sectional view of the exemplary embodiment of FIG. 9.
Figure 11:
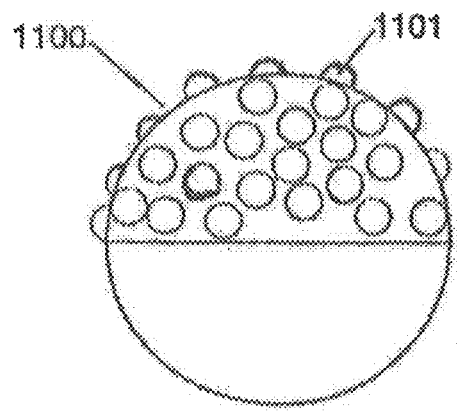
FIG. 11 is an exemplary view showing a shape of a massager according to an alternative embodiment of the present disclosure.
Figure 12:
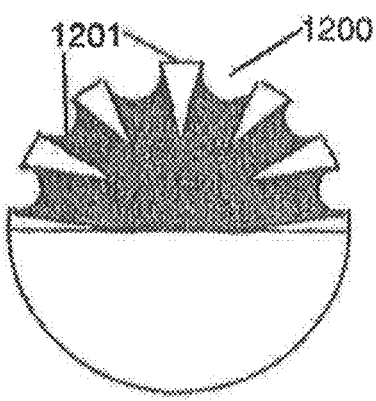
FIG. 12 is another exemplary view showing a shape of a massager according to an alternative embodiment of the present disclosure.
Figure 13:
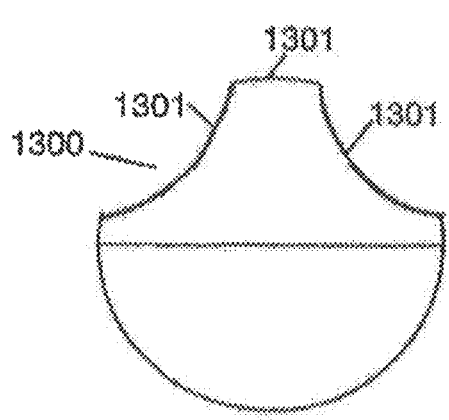
FIG. 13 is still another exemplary view showing a shape of a massager according to an alternative embodiment of the present disclosure.
Figure 14:
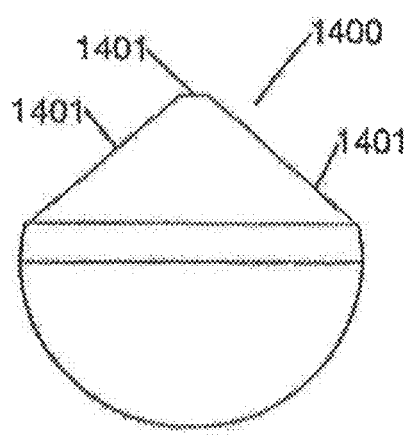
FIG. 14 is yet another exemplary view showing a shape of a massager according to an alternative embodiment of the present disclosure.

As shown in FIG. 9, the body has first and second portions 350a, 350b (see FIG. 2) that are separable. A proximal end of the first mounting frame 205a is attached to the interior surface 250 of the first portion 350a and a distal end extends beyond the circular distal flange 235a to form a shoulder 236a. In addition, a proximal end 245b of the second mounting frame 205b attaches to the interior surface 250 of the second portion 350b and a distal end extends beyond the circular distal flange 235b to form a shoulder 236b, The shoulders 236a, 236b abut when the body is assembled, which then causes a recess 905 to form.

Further, foam washers 103a, 103b may be inserted between the first and second portions 350a, 350b. When the foam washers 103a, 103b are inserted between the first and second portions 350a, 350b, the foam washers 103a, 103b are compressed within the recess 905 that is formed by the shoulders 236a, 236b.

The body 105 may include a female portion that has a circumferential groove near an edge of the female portion and a male portion that has a circumferential ridge near an edge of the male portion. The edges may be configured to align so that the circumferential ridge fits within the circumferential groove to keep the portions together and form the body. More specifically, the female portion and the male portion snap together to form the body 105 of the thermal massaging apparatus 100. In addition, a shape of the portions may be selected from the group consisting of hemispherical, a cross-sectional trapezoidal shape, a flattened pyramid, a cross-sectional rectangular shape and combinations thereof.

The body may also include a first hemisphere and a second hemisphere that threads to the first hemisphere to selectively enclose the interior. In other words, the first hemisphere and the second hemisphere screw together to form the body 105 of the thermal massaging apparatus 100.

As shown in FIG. 2, the elongated rod 405 may include a tubular body 406 that has a convex end 420 that has a convex shape and a concave end 425 having a concave shape so that, depending upon the shape of the tissue needing massage, one end of the massaging rod is complementarily shaped. The convex end 420 and the concave end 425 are designed to selectively couple with the corresponding mounting frame 205a, 205b.

More specifically, the elongated rod 405 may have a first O-ring 440 located on the convex end 420 of the elongated rod 405 and a second O-ring 445 located on the concave end 425 of the elongated rod 405. When the body 105 is formed, the interior surface 250 applies pressure to the first O-ring 440 and the second O-ring 445 to deform the O-rings 440,445 and keeps the body 105 intact. The pressure applied to the O-rings 440, 445 helps maintain the body together until an external force is applied (e.g., a user pulling the body apart).

The tubular body 406 defines an interior that houses a filler material that retains cold when exposed to cold temperatures or other cooling methods (e.g., an acetone water solution). Alternatively, the interior houses a filler material that retains heat when exposed to hot temperatures or other heating methods.

Further, the elongated rod 405 may be made of thermoresistant plastic or any other rigid material with thermosresistant properties such as one selected from the group consisting of metal, rubber, and a combination thereof. The tube 415 may have an exterior diameter of about 0.45 inches to about 1.2 inches.

Furthermore, the body 105 may have a spherical shape. When the body has a spherical shape, the elongated rod 405 is located along one axis within the spherical body where the axis is a maximum diameter of the body. The maximum diameter of the body may vary from about 1.5 inches to about 4 inches. The different maximum diameters may allow the thermal massaging apparatus to for different therapeutic purposes.

Turning to FIGS. 11-14, additional embodiments of the massager of the present disclosure are indicated generally by the reference numerals 1100, 1200, 1300, 1400, respectively. The massagers 1100, 1200, 1300, 1400 are very similar to the massagers described above, and therefore like reference numerals are used to indicate like elements. The primary difference of the massagers 1100, 1200, 1300, 1400 in comparison to the massagers above is the outer shape. The massagers 1100, 1200 can provide additional features 1101, 1201 that increase and/or vary applied pressure. The outer shape can also vary to provide surfaces 1301, 1401 that complimentarily engage various body parts. As shown, only half of the massagers 1100, 1200, 1300, 1400 is modified. It is envisioned that more or less, even all, of the massagers 1100, 1200, 1300, 1400 may be varied depending upon the anticipated usage.

Figure 15:
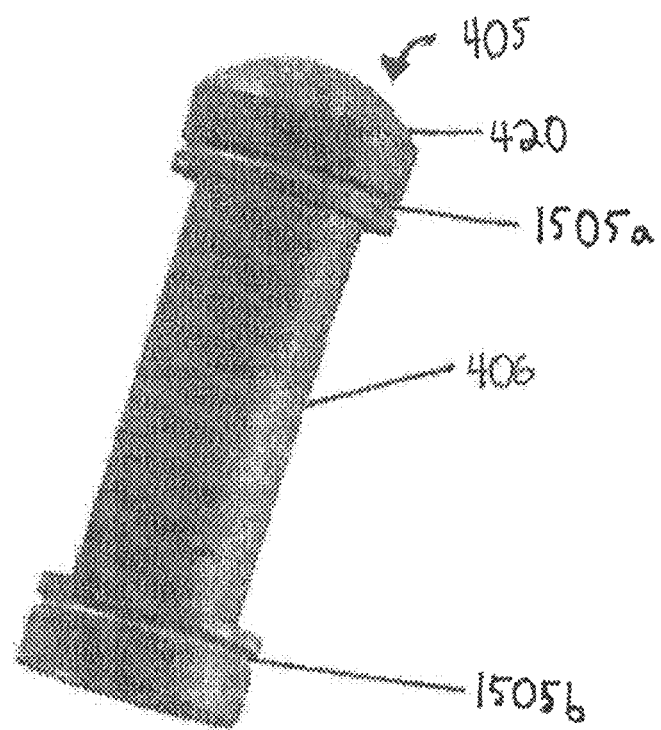
FIG. 15 is a sub-assembly of a thermal massaging rod according to an alternative embodiment of the present disclosure.
Figure 16:
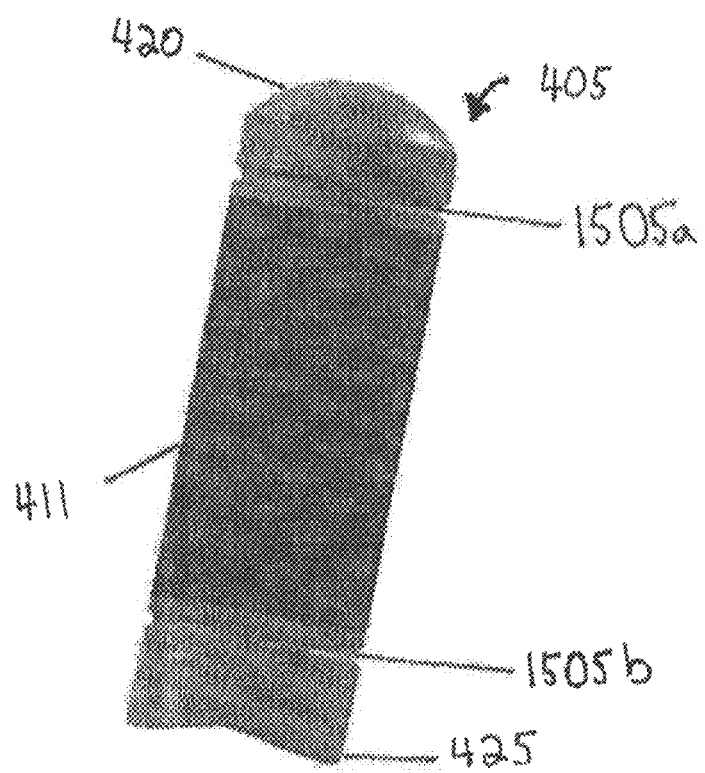
FIG. 16 is a fully assembled thermal massaging rod according to an alternative embodiment of the present disclosure.

As illustrated in FIGS. 15 and 16, according to another embodiment of the present disclosure, a thermal massaging rod 405 may include a tubular body 406 having a convex end 420 that has a convex shape and a concave end 425 having a concave shape. The convex end 420 and the concave end 425 may be used to massage different part of the human body where either the convex end 420 or the concave end 425 may be more advantageous to rehabilitation. Further, a circumferential recess 1505a, 1505b may be formed on the convex end 420 and the concave end 425. The circumferential recesses 1505a, 1505b are used to hold the O-rings 440,445 in place for use with a further embodiment of the present disclosure.

The thermal massaging rod 405 may also include a filler material 410 within the interior that retains cold when exposed to cold temperatures or other cooling methods (e.g., an acetone water solution). Alternatively, the interior may contain a filler material 410 that is able to retain heat when exposed to hot temperatures or heating methods (e.g., microwaving).

Further, the thermal massaging rod 405 may be made of a thermos-resistant plastic or any other rigid material with thermos-resistant properties such as one selected from the group consisting of metal, rubber, and a combination thereof.

The thermal massaging rod may also include a sleeve 411 wrapped around the tubular body 406. The sleeve may be made of a material that does not become cold when exposed to substantially low temperatures such as one selected from the group consisting of thermos-resistant rubber, neoprene, and foam. The sleeve 411 allows a person to more comfortably use the thermal massaging rod 405 without substantial undesired exposure to decreased temperatures.

An aspect of the present disclosure provides a thermal massaging apparatus that may further stimulate injury rehabilitation over using merely ice or massage, individually. Rather, exemplary embodiments of the present disclosure may combine the effects of ice and massage to decrease pain, inflammation, and swelling and remodel damaged tissue to allow for more efficient healing. In addition, the thermal massaging apparatus may prevent frostbite on an injured area of a human body.

As described above, although the present disclosure has been described with reference to exemplary embodiments and the accompanying drawings, it would be appreciated by those skilled in the art that the present disclosure is not limited thereto but various modifications and alteration may be made without departing from the scope defined in the following claims.

We claim:

1. A thermal massaging apparatus, comprising:
    a body having first and second complementary halves, each half having an exterior surface surrounding an interior surface, the interior surface defining a first interior;
    a first mounting frame extending from the interior surface of the first complementary half;
    a second mounting frame opposing the first mounting frame and extending from the interior surface of the second complementary half;
    an elongated rod comprising a tube with a first end and a second end,
    wherein: the first end of the tube selectively couples to the first mounting frame and has a convex shape configured to massage a first type of body contour;
    the second end selectively couples to the second mounting frame and has a concave shape configured to massage a second type of body contour; and when the first and second halves are coupled together, the elongated rod extends from within the first mounting frame to within the second mounting frame,
    wherein the first and second mounting frame each define a second interior;
    a first O-ring coupled to the first mounting frame;
    a second O-ring coupled to the second mounting frame so that the first and second O-rings are compressed upon contact with the elongated rod to retain the complementary halves together; and
    a filler material that retains thermal energy within at least one of the first and second interiors,
    wherein the exterior surface of one or both complementary halves and the elongated rod are configured to massage tissues in arrangements including: the elongated rod alone; either the first or second half alone; the first and second half joined together via the elongated rod such that the elongated rod is completely enclosed by the second interior; the convex end of the elongated rod after coupling of the concave end to the second mounting frame; and the concave end of the elongated rod after coupling of the convex end to the first mounting frame.

2. The thermal massaging apparatus according to claim 1, wherein a shape of each of the complementary halves is one selected from the group consisting of hemispherical, a cross-sectional trapezoidal shape, a flattened pyramid, hemisphere with bumps, hemisphere with ridges, a cross-sectional plateau shape and combinations thereof.

3. The thermal massaging apparatus according to claim 2, wherein one of the complementary halves has a cross-sectional rectangular shape and a cross-sectional trapezoidal shape.

4. The thermal massaging apparatus according to claim 3, wherein the body is spherical and the tube extends along an axis on a maximum diameter of the body.

5. The thermal massaging apparatus of claim 1, wherein the selective coupling of either the convex end or the concave end to either the first or second mounting frame occurs through compression of either the first or second O-ring.

6. The thermal massaging apparatus of claim 1, wherein either the convex end or the concave end abuts the first or second mounting frame upon coupling.

7. A thermal massaging apparatus, comprising:
    a body having:
        an exterior surface surrounding an interior surface, the interior surface defining a first interior;
        a first portion; and
        a second portion, wherein the first and second portions are separable;
    a first mounting frame extending from the interior surface;
    a second mounting frame opposing the first mounting frame and extending from the interior surface;
    an elongated rod with a concave end and a convex end extending between the first mounting frame and the second mounting frame, the first and second mounting frames defining a second interior;
    a first O-ring coupled to the first mounting frame;
    a second O-ring coupled to the second mounting frame so that the first and second O-rings are compressed upon contact with the elongated rod to retain the elongated rod in the second interior; and
    a filler material that retains thermal energy within at least one of the first and second interiors,
    wherein the exterior surface of the body and the elongated rod are configured to massage tissues in arrangements including: the elongated rod alone; either the first portion or second portion alone; the first portion and the second portion joined together via the elongated rod such that the elongated rod is completely enclosed by the second interior; the convex end of the elongated rod after coupling of the concave end to the second mounting frame; and the concave end of the elongated rod after coupling of the convex end to the first mounting frame.

8. The thermal massaging apparatus according to claim 7, the first mounting frame includes a proximal end attached to the interior surface of the first portion and a distal end that forms a first shoulder, the second mounting frame includes a proximal end attached to the interior surface of the second portion and a distal end that forms a second shoulder, further comprising:

a foam washer between the first and second portions, wherein when assembled, the shoulders abut to form a recess between the first and second portions and the foam washer is compressed within the recess.

9. The thermal massaging apparatus according to claim 8, wherein the first portion is a first hemisphere and the second portion is a second hemisphere that threads to the first hemisphere to selectively enclose the first and second interior.

10. The thermal massaging apparatus according to claim 9, wherein the interior portion of one of the first hemisphere and the second hemisphere has a cross-sectional rectangular shape.

11. The thermal massaging apparatus according to claim 9, wherein the first mounting frame includes a first circular flange and the second mounting frame includes a second circular flange.

12. The thermal massaging apparatus according to claim 11, wherein the elongated rod includes a tube having a first end that is the convex end and is configured to massage a first type of body contour in contact with the first circular flange and a second end that is the concave end and is configured to massage a second type of body contour in contact with the second circular flange.

13. The thermal massaging apparatus according to claim 12, wherein the body is spherical and the tube extends along an axis on a maximum diameter of the body.

14. The thermal massaging apparatus according to claim 7, wherein the body includes:
 a female portion defining a circumferential groove adjacent an edge of the female portion; and
 a male portion defining a circumferential ridge adjacent an edge of the male portion;
wherein the edges align so that the circumferential ridge selectively couples in the circumferential groove to retain the portions together.

15. The thermal massaging apparatus according to claim 14, wherein a shape of each of the first and second portions of the body is selected from the group consisting of hemispherical, a cross-sectional trapezoidal shape, a flattened pyramid, and combinations thereof.

16. The thermal massaging apparatus according to claim 14, wherein an interior portion of one of the female portion and the male portion has a cross-sectional rectangular shape and a cross-sectional trapezoidal shape.

17. The thermal massaging rod according to claim 7, further comprising a filler material within the tube that retains cold when exposed to cold temperatures.

18. The thermal massaging rod according to claim 7, further comprising a foam cylinder wrapped around the tube.

19. A massaging apparatus, comprising:
 a body having first and second complementary halves, each half having an exterior surface surrounding an interior surface, the interior surface defining a first interior;
 a first mounting frame extending from the interior surface of the first complementary half;
 a second mounting frame opposing the first mounting frame and extending from the interior surface of the second complementary half;
 an elongated rod comprising a tube with a first end and a second end,
 wherein: the first end of the tube selectively couples to the first mounting frame and has a convex shape configured to massage a first type of body contour;
 the second end selectively couples to the second mounting frame and has a concave shape configured to massage a second type of body contour; and when the first and second halves are coupled together, the elongated rod extends from within the first mounting frame to within the second mounting frame,
 wherein the first and second mounting frame each define a second interior;
 wherein the exterior surface of one or both complementary halves and the elongated rod are configured to massage tissues in arrangements including: the elongated rod alone; either the first or second half alone; the first and second half joined together via the elongated rod such that the elongated rod is completely enclosed by the second interior; the convex end of the elongated rod after coupling of the concave end to the second mounting frame; and the concave end of the elongated rod after coupling of the convex end to the first mounting frame.

20. The massaging apparatus of claim 19, wherein the selective coupling of either the convex end or the concave end to either the first or second mounting frame occurs through compression of either the first or second O-ring, and either the convex end or the concave end abuts the first or second mounting frame upon coupling.

* * * * *